(12) United States Patent
Hoang et al.

(10) Patent No.: US 8,013,122 B2
(45) Date of Patent: Sep. 6, 2011

(54) METHOD OF PURIFYING APOLIPOPROTEIN A-1

(76) Inventors: Kieu Hoang, Agoura Hills, CA (US); Bao Xiangfei, Shanghai (CN)

( * ) Notice: Subject to any disclaimer, the term of this patent is extended or adjusted under 35 U.S.C. 154(b) by 0 days.

(21) Appl. No.: 12/457,796

(22) Filed: Jun. 22, 2009

(65) Prior Publication Data

US 2009/0286960 A1 Nov. 19, 2009

Related U.S. Application Data

(63) Continuation-in-part of application No. PCT/US2007/020258, filed on Sep. 19, 2007.

(30) Foreign Application Priority Data

Dec. 20, 2006 (CN) ............ 2006 1 0147503

(51) Int. Cl.
   *C07K 1/00* (2006.01)
(52) U.S. Cl. .......... 530/359; 530/350; 530/300; 435/7.1
(58) Field of Classification Search .................. None
    See application file for complete search history.

(56) References Cited

U.S. PATENT DOCUMENTS

| | | | |
|---|---|---|---|
| 5,525,472 A | 6/1996 | Lifshitz et al. | |
| 5,747,455 A | 5/1998 | Wainwright et al. | |
| 5,834,596 A | 11/1998 | Ageland et al. | |
| 6,090,921 A * | 7/2000 | Winge et al. | 530/359 |
| 6,222,021 B1 | 4/2001 | Wainwright et al. | |
| 6,423,830 B1 * | 7/2002 | Winge et al. | 530/359 |
| 6,602,694 B1 | 8/2003 | Albrant et al. | |
| 2006/0014692 A1 | 1/2006 | Zhu et al. | |
| 2006/0025575 A1 | 2/2006 | Korth et al. | |

FOREIGN PATENT DOCUMENTS

EP 0333474 9/1989

OTHER PUBLICATIONS

Sanz et al., A New Vaccinia Virus Intermediate Transcription Factor. J. Virol. Aug. 1998, 72(8):6880-6883; p. 6881, Paragraph 2 to p. 6882, paragraph 1.
Mezdour et al., Journal of Chromatography, 414(1987) 35-45; Anion-Exchange Fast Protein Liquid Chromatographic Characterizaton and Purification of Apolipoproteins A-1.
Tricerri et al., IJBC, 1994, vol. 1, pp. 159-166; A Rapid and Efficient Procedure for the Purification of Human Apolipoprotein A-1 Using Gel Filtration HPLC.

* cited by examiner

*Primary Examiner* — Hope Robinson
(74) *Attorney, Agent, or Firm* — Merek, Blackmon & Voorhees

(57) ABSTRACT

A first method of purifying apolipoprotein A-1 includes mixing plasma fraction IV with a 1-8 M urea solution to form a pretreatment solution; loading the pretreatment solution to a first anion chromatography column, and then eluting to obtain an apoA-1 protein solution; and loading the apoA-1 protein solution to a second anion chromatography column, and eluting to obtain pure apoA-1 protein. A second method includes dissolving plasma fraction IV in a buffer to produce a pretreatment solution; adding NaCl to the pretreatment solution and cooling it to form apoA-1 precipitate; collecting and reconstituting the apoA-1 precipitate; loading the reconstituted apoA-1 to an anion exchange column; and eluting apoA-1 from the column.

33 Claims, 6 Drawing Sheets

METHOD OF PURIFYING APOLIPOPROTEIN A-1

CROSS REFERENCE TO RELATED APPLICATIONS

This is a continuation-in-part of International Application PCT/US2007/020258, with an international filing date of Sep. 19, 2007. The applicants hereby claim the priority under 35 U.S.C. 119 of Application No. 200610147503.7, filed in the People's Republic of China on Dec. 20, 2006, the priority of which is claimed in International Application PCT/US2007/020258.

FIELD OF THE INVENTION

The present invention relates to protein preparation, and especially the preparation of apoA-1.

BACKGROUND OF THE INVENTION

High Density Lipoprotein (HDL) is an important lipoprotein in blood. It participates in a process called Reverse Cholesterol Transport (RCT), through which cholesterol in tissue cells can be transported to the liver to be metabolized into a harmless substance, hence restraining the occurrence and evolution of atherosclerosis (AS). Apolipoprotein A-1 (apoA-1) is the main form of apolipoprotein in High Density Lipoprotein (HDL). It is closely related to the physiological function of HDL in the blood. It is the main undertaker of the HDL anti-atherosclerosis function. Besides, according to recent research results, apoA-1 deficiency may cause the evolution of atherosclerosis and an increase of inflammation. Furthermore, apoA-1 decreases Low Density Lipoproteins (LDL) and cleans plaque. In addition, according to recent research results, apoA-1 is promising for applications in drugs with an anti-inflammation effect or liver-targeting function.

Methods such as ultra-speed centrifuge, organic solvent precipitation, and high performance liquid chromatography (HPLC) are usually used to purify apoA-1. However, there are some innate defects in these methods, such as low yield, high cost, insecurity, and a production scale that is too small. These methods are not suitable for apoA-1 industrial production.

On the other hand, as one of the fractions acquired after plasma fractionation, plasma fraction IV is always discarded because no useful product can be purified for commercial application. In accordance with the present invention, a purification method suitable for large-scale production is provided, and apoA-1 with high purity is acquired from plasma fraction IV.

SUMMARY OF THE INVENTION

According to one method of the present invention, it was found that urea can dramatically influence the behavior of apoA-1 in ion exchange chromatography. When apoA-1 is not combined with urea, it is very easily absorbed on an anion exchange column and relatively difficult to be eluted off the column. However, when apoA-1 is combined with urea, it is very easy to be eluted off an anion exchange column. Therefore, according to one method of the present invention, apoA-1 is purified by two anion exchange columns, using two different elution profiles.

The aforementioned method of the present invention for purifying apolipoprotein A-1, including the following steps: a) plasma fraction IV (acquired by the Cohn Ethanol Fractionation method) is mixed with a 1-8 M urea solution, forming a fraction IV pretreatment solution; b) the pretreatment solution acquired in step a is loaded to a first anion chromatography column, and then eluted by a 1-8 M urea solution to obtain apoA-1 protein; c) apoA-1 protein solution from step b is loaded in a second anion chromatography column, and then eluted by 0-1 M urea solution to obtain pure apoA-1 protein. This method has advantages such as high yield, low cost, and suitability for industrial production. Besides, this method uses plasma fraction IV as its raw material, thereby making full use of plasma resources.

According to an alternate method of the present invention, apoA-1 precipitate is obtained, and the apoA-1 is purified by just one anion exchange column. The yield of apoA-1 from the alternate method of the present invention is 500-600 grams per ton of plasma, which is much higher than the yield of the first-described method according to the present invention, and the production cycle of the alternate method is decreased to less than one half the production cycle of other methods for purifying apoA-1.

The pure apoA-1 acquired in this invention is promising for applications in atherosclerosis treatment, anti-inflammation treatment, antitoxin treatment, liver-targeting drugs, etc.

DETAILED DESCRIPTION OF THE DRAWINGS

DETAILED DESCRIPTION OF THE PREFERRED EMBODIMENTS

Figure 1:
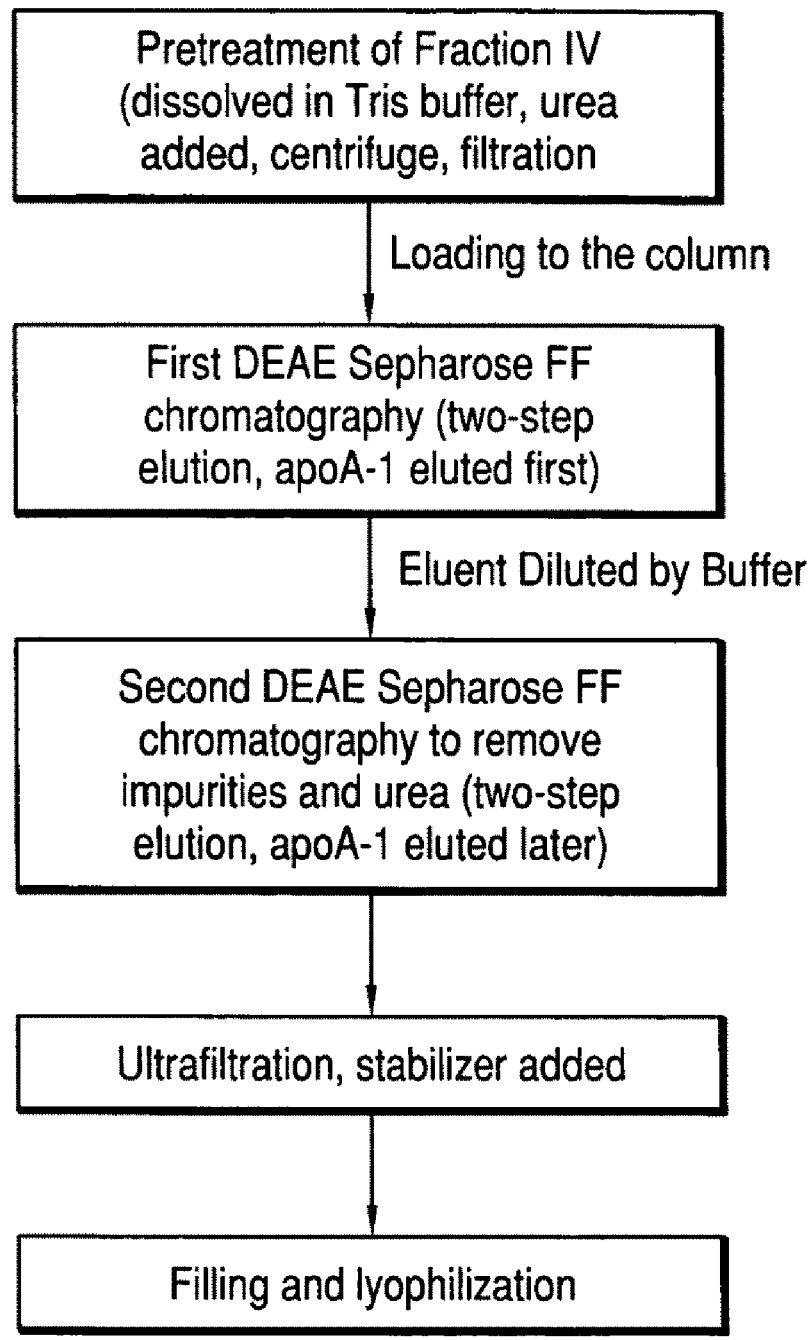
FIG. 1 is a flow chart showing a first production process according to the present invention of apoA-1 from plasma fraction IV.

A first process according to the present invention is illustrated in FIG. 1, which is a flow chart showing the production process of apoA-1 from plasma fraction IV.

Plasma Fraction IV Pretreatment

The fraction IV described is acquired by the Cohn Ethanol Fractionation method (Cohn, E. J.; Strong, L. E.; Huges, W. L.; et al., Preparation and properties of serum and plasma proteins IV. A system for the separation into fractions of the protein and lipoprotein components of biological tissues and fluids. Amer Chem Soc., 1946, 68:459-475). The fraction IV is dissolved in a buffer, and a certain amount of urea is added to the solution and mixed thoroughly. In this process the apoA-1 is combined with urea, and this combination is reversible. The concentration of the urea added is 1-8 M, preferably 3-7 M, and more preferably 5-6 M. The mass ratio of the fraction IV and the urea is 1:30-300, preferably 1:90-240, and more preferably 1:150-210.

A buffer that is usually used in this field was chosen: Tris buffer, phosphate buffer or HEPES buffer, preferably Tris buffer. The buffer pH is 7.2-8.5, preferably 7.5-8, and more preferably 7.8.

In another example, the fraction IV is dissolved under low temperature (0-4° C.).

In another example, the pretreatment solution is centrifuged to remove sediments, and then filtered. The centrifuge speed is 6,000-10,000 rpm, preferably 8,000 rpm, and the pore size of the filtration membrane is 0.2-0.6 µm, preferably 0.45 µm.

The First DEAE Anion Exchange Chromatography

The solution obtained in step (1) is loaded to a DEAE (Diethylamino Ethanol) anion exchange column, and protein in the solution, including apoA-1, is combined onto the column. More specifically, the apoA-1 solution acquired in step (1) is diluted with water 1-10 fold, and preferably 3-7 fold. After dilution, the solution is loaded onto the anion exchange column at a flow rate of 0.5-1.5 ml/min, preferably 0.8-1.2 ml/min.

Then, the protein is eluted by two elution steps. In the first step, a buffer with low conductivity is used to elute the column. ApoA-1 combines with the column weakly at this time, and protein mainly containing apoA-1 can be eluted first. In the second step, a buffer with high conductivity is used to elute the column, and protein mainly containing impurities is eluted.

The eluent that elutes apoA-1 contains 1-8 M urea, preferably 3-7 M, and more preferably 5-6 M. The conductivity is 1-4 ms/cm, preferably 2-3.8 ms/cm, and more preferably 2.5-3.6 ms/cm. Salts in the eluent may include, but are not limited to, NaCl, KCl, $MgCl_2$ and $CaCl_2$. NaCl is preferred.

The eluent that elutes impurities contains 0-1 M urea; 0 M is preferred. The conductivity is 4.5-100 ms/cm. Salts in the eluent may include, but are not limited to, NaCl, KCl, $MgCl_2$ and $CaCl_2$. NaCl is preferred.

A buffer usually used in this field is chosen: Tris buffer, phosphate buffer or HEPES buffer, preferably Tris buffer. The buffer pH is 7.2-8.5, preferably 7.5-8, and more preferably 7.8

The column flow rate of the fraction pretreatment solution obtained in step 1 is 0.5-1.5 ml/min, preferably 0.8-1.2 ml/min. The volume ratio of fraction IV and the column is 1:5-50, preferably 1:15-40, and more preferably 1:20-30.

The Second DEAE Anion Exchange Chromatography

The apoA-1 solution acquired in the first DEAE anion exchange chromatography step, containing apoA-1, urea and a slight amount of impurities, is diluted by water to a lower conductivity and then loaded onto a second DEAE column.

The protein is combined on the second DEAE column, and the urea remains in the solution and is eliminated as flow-through. Then, the protein is eluted by two elution steps. In the first step, a buffer with relatively low conductivity is used to elute the column. ApoA-1 strongly combines with the column, and the impurities are eluted off the column. In the second step, a buffer with higher conductivity is used to elute the column, and pure apoA-1 is eluted.

The conductivity of the eluent that elutes the impurities is 1-20 ms/cm, preferably 7-15 ms/cm, more preferably 9-12 ms/cm. 0-1 M urea may exist in the eluent, and 0 M is preferred. Salts in the eluent may include, but are not limited to, NaCl, KCl, $MgCl_2$ and $CaCl_2$. NaCl is preferred.

The conductivity of the eluent that elutes the apoA-1 is 50-100 ms/cm, preferably 70-95 ms/cm, and more preferably 80-90 ms/cm 0-1 M urea may exist in the eluent, and 0 M is preferred. Salts in the eluent may include, but are not limited to, NaC, KCl, $MgCl_2$ and $CaCl_2$. NaCl is preferred.

In another example, after apoA-1 and a slight amount of impurities are combined on the second DEAE column, a conductivity gradient of 3 ms/cm/min is applied to elute the protein. The conductivity of the eluent rises from 1 to 100 ms/cm. Pure apoA-1 is eluted at a conductivity between 30 and 60 ms/cm and collected.

A buffer usually used in this field is chosen: Tris buffer, phosphate buffer or HEPES buffer, preferably Tris buffer. The buffer pH is 7.2-8.5, preferably 7.5-8, more preferably 7.8.

In this method according to the present invention, post processing methods are also provided to process the pure apoA-1 solution acquired in step (3). The methods include an ultra-filtration step, a stabilizer adding step, and a lyophilization step. Freeze dried apoA-1 is ultimately acquired after post processing steps.

Ultra-filtration, which is frequently applied in this field, is used for apoA-1 solution conditioning, adjusting the solution to an appropriate pH and protein concentration. For the ultra-filtration, a Millipore PES ultra-filtration membrane with a molecular weight cutoff of 5000 is used, the working temperature is 4° C., and the working pressure is under 0.3 Mpa.

The stabilizer added is from among those frequently used in this field, including, but not limited to, hydroxypropyl cellulose, hydroxypropyl methylcellulose, sodium cellulose glycolate, sucrose, sorbierite, etc.

A freeze drying method that is frequently applied in this field is used: the product is frozen below −36° C. for 3-4 hours, and then freeze dried under a vacuum of 7-9 Pa. The temperature in the cold trap is about −55° C., and then, in a second period, the shelf temperature is 40° C. and the time is about 15 hours.

The chromatography columns used in this invention may be from among those frequently applied in this field, and the chromatography media may be QAE (quaternary amine) or DEAE anion exchange chromatography media, preferably DEAE.

The invention is further illustrated in detail in the following examples. It should be understood that these examples are used to explain the invention but not to limit the scope of the invention. For those experiments in the following examples, if a condition is not specified, it means that the condition is routine or advised by the manufacturer. Unless otherwise specified, the ratios mentioned below are mass ratios.

Unless defined otherwise, the definitions of the technical or scientific terms are those generally understood by the technician of ordinary skill in this field.

Example 1

ApoA-1 Purification

The starting materials include: 0.2 g plasma fraction IV, two 5 ml DEAE anion exchange columns (from GE Healthcare), and purification and conductivity determination equipment, namely, an AKTA EXPLORER 100 (from GE Healthcare).

Plasma Fraction IV Pretreatment 0.2 g of fraction IV is dissolved in 100 ml Tris buffer (pH 7.8, 4° C.). Urea is added to the solution until the end concentration reaches 6 mol/L and is mixed thoroughly. The solution is centrifuged at 8,000 rpm to remove sediment, then filtrated by a 0.45 µm filter.

The First DEAE Anion Exchange Chromatography

Figure 2:
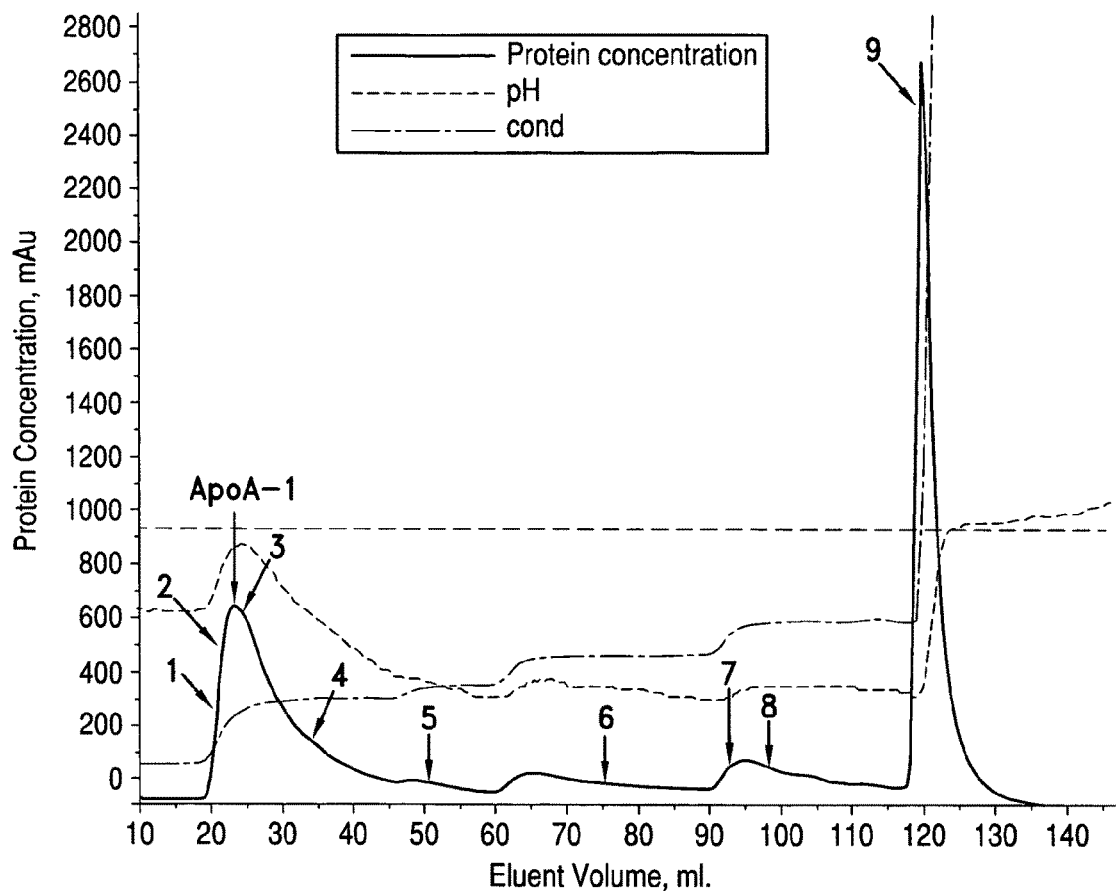
FIG. 2 shows the elution process of the first ion exchange chromatography in Example 1.
Figure 3:
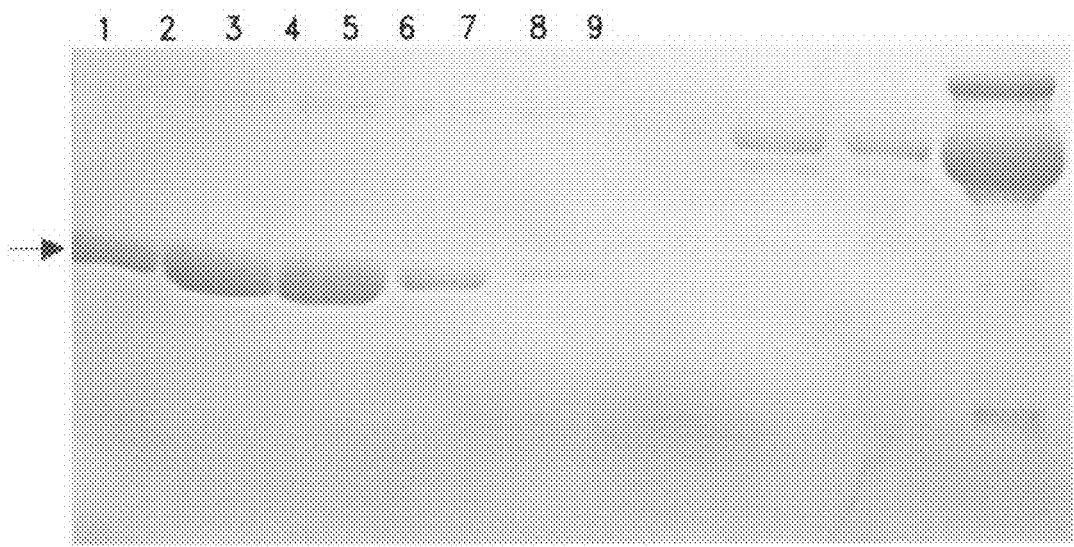
FIG. 3 shows the SDS-PAGE electrophoresis result of the sample taken in the first ion exchange chromatography in Example 1.

A first DEAE column is equilibrated by Tris buffer (pH 7.8) containing 6 mol/L urea. The solution from step (1) is loaded onto the DEAE column at a flow rate of 1 ml/min. Tris buffer (pH 7.8, conductivity 3.5 ms/cm) with a urea concentration of 6 mol/L is used to elute the column. ApoA-1 is eluted. The eluted volume is 20 ml. Four different Tris buffers (each with pH 7.8, and with conductivities of 4.3 ms/cm, 5.4 ms/cm, 6.7 ms/cm, and 59.2 ms/cm, respectively) are used to elute the column, and the impurities are eluted. The elution process and SDS-PAGE electrophoresis results are shown in FIGS. 2 and 3, respectively. The x-coordinate in FIG. 2 is the elute volume in the chromatography process, and the y-coordinate is the protein concentration in the elute. The numbers 1 to 9 indicate the spots where the sample is taken. The sample is determined by SDS-PAGE electrophoresis in FIG. 3. The arrow shows the position of the apoA-1 protein.

The Second DEAE Anion Exchange Chromatography

The apoA-1 eluted in step (2) (pH 7.8, conductivity 3.5 ms/cm), containing apoA-1, urea and slight amount of impurities, is diluted with water by 5 fold and loaded into the second DEAE column at a flow rate of 10 ml/min. ApoA-1 and a slight amount of impurities are combined on the column, and urea remains in the solution and is removed as flow-through.

Tris buffer without urea (pH 7.8, conductivity 11.7 ms/cm) is used to elute the column, and the impurities are eluted off the column. Then, Tris buffer without urea (pH 7.8, conductivity 85.2 ms/cm) is used to elute the column, and apoA-1 is eluted off.

Figure 4:
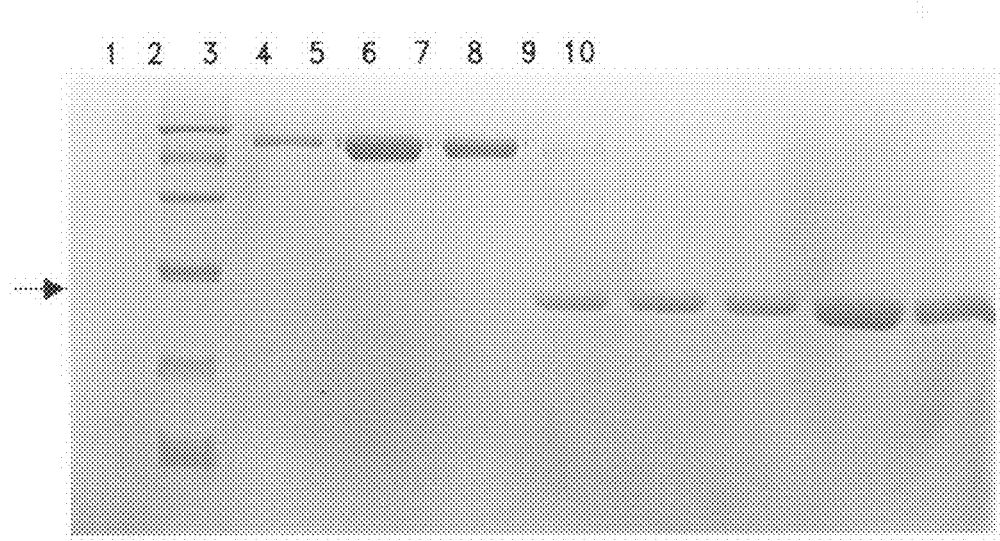
FIG. 4 shows the SDS-PAGE electrophoresis result of the sample taken in the second ion exchange chromatography in Example 1.

The SDS-PAGE electrophoresis results show that pure apoA-1 is acquired in this step (FIG. 4). The sample 1 is the protein in the column flow-though solution during the loading process. The sample 2 is the protein mark. The numbers 3 to 5 indicate the sample collected during the first elution process, which mainly consists of impurities. The numbers 6 to 10 indicate the sample collected during the second elution process, which mainly consists of apoA-1. Samples 6 and 7 are diluted by 5 fold, and sample 8 is diluted by 10 fold. The arrow shows the position of apoA-1 protein.

Example 2

ApoA-1 Purification

The 0.2 g of plasma fraction IV and the equipment are the same as those in Example 1.

Plasma Fraction IV Pretreatment

The 0.2 g of fraction IV is dissolved in 100 ml Tris buffer (pH 7.8, 4° C.). Urea is added to the solution until the end concentration reaches 6 mol/L, and the solution is mixed thoroughly. The solution is centrifuged at 8,000 rpm to remove the sediment and then filtrated by a 0.45 μm filter.

The First DEAE Anion Exchange Chromatography

The first DEAE column is equilibrated by Tris buffer (pH 7.8) containing 1 mol/L urea. The solution from step (1) is loaded onto the first DEAE column at a flow rate of 1 ml/min. Tris buffer (pH 7.8, conductivity 3.5 ms/cm) with a urea concentration of 1 mol/L is used to elute the column. ApoA-1 is eluted. The elute volume is 20 ml. Tris buffer (pH 7.8, 59.2 ms/cm respectively) is used to elute the column, and the impurities are eluted.

The Second DEAE Anion Exchange Chromatography

Figure 5:
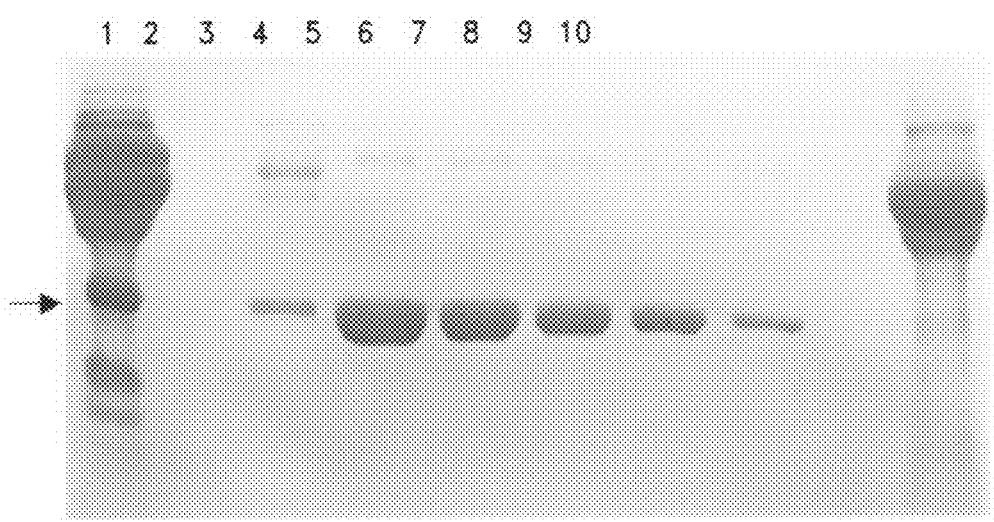
FIG. 5 shows SDS-PAGE electrophoresis result of the sample taken in Example 4.
Figure 6:
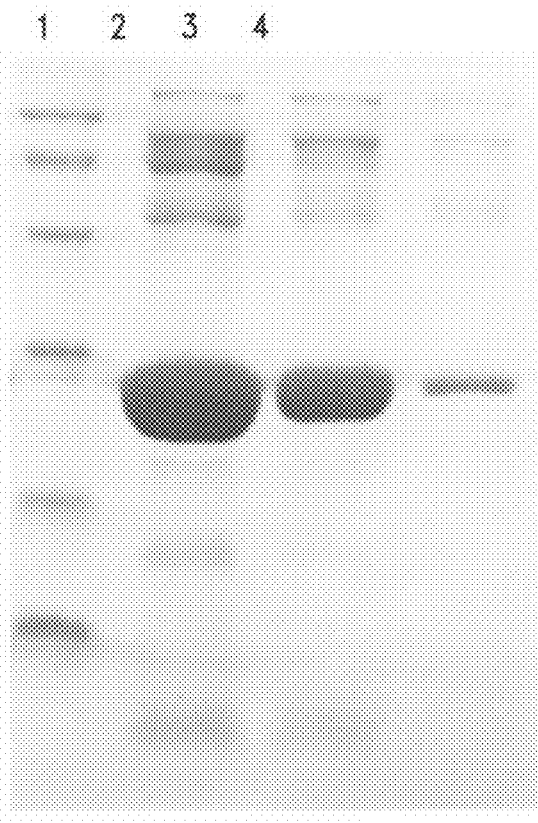
FIG. 6 shows SDS-PAGE electrophoresis result of the sample taken in Example 2.

The procedures are the same as in Example 1. The purification results are shown in FIG. 5. Sample 1 is the supernatant of plasma fraction IV after the pretreatment process. Samples 4 to 8 are apoA-1 collected in the purification process. Sample 10 is the impurities collected during the purification process. The arrow shows the position of apoA-1 protein.

Example 3

ApoA-1 Purification

The 0.2 g of plasma fraction IV and the equipment are the same as those in Example 1.

Plasma Fraction IV Pretreatment

The 0.2 g of fraction IV is dissolved in 100 ml Tris buffer (pH 7.8, 4° C.). Urea is added to the solution until the end concentration reaches 6 mol/L, and the solution is mixed thoroughly. The solution is centrifuged at 8,000 rpm to remove the sediment and then filtrated by the 0.45 μm filter.

The First DEAE Anion Exchange Chromatography

The first DEAE column is equilibrated by Tris buffer (pH 7.8) containing 8 mol/L urea. The solution from step (1) is loaded onto the DEAE column at a flow rate of 1 ml/min. Tris buffer (pH 7.8, conductivity 3.5 ms/cm) with 8 mol/L urea is used to elute the column. ApoA-1 is eluted. The elute volume is 20 ml. Tris buffer (pH 7.8, conductivity 59.2 ms/cm) is used to elute the column, and the impurities are eluted.

The Second DEAE Anion Exchange Chromatography

Figure 7:
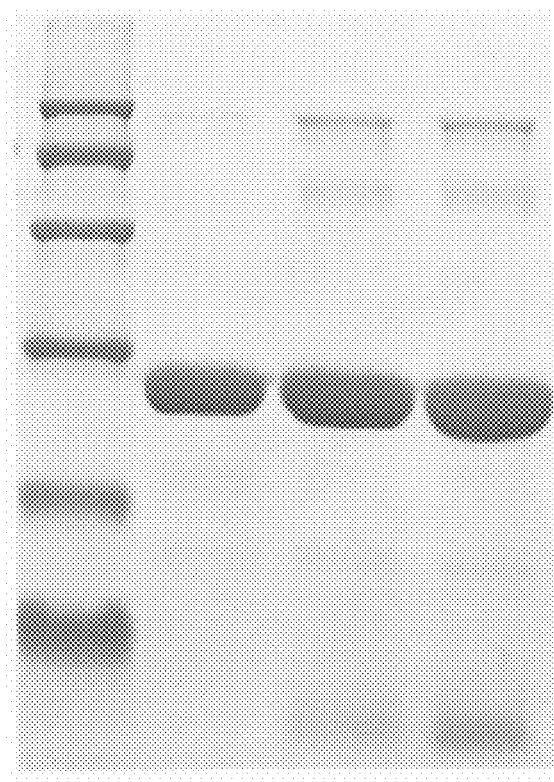
FIG. 7 shows SDS-PAGE electrophoresis result of the sample taken in Example 3.

The procedures are the same as in Example 1. The purification results are shown in FIG. 7.

Example 4

ApoA-1 Pilot Scale Purification

The starting materials include: 60 g of plasma fraction IV, two 1500 ml ion exchange columns (from Shanghai Jinhua Chromatography Equipment Cooperation), anion exchange media, namely, DEAE Sepharose FF (from GE Healthcare), a pump and a UV detector (from Shanghai Jinhua Chromatography Equipment Corporation), and conductivity determination equipment, namely, an AKTA EXPLORER 100 (from GE Healthcare)

Plasma Fraction IV Pretreatment 60 g fraction IV is dissolved in 100 ml Tris buffer (pH 7.8, 4° C.). Urea is added to the solution until the end concentration reaches 6 mol/L, and the solution is mixed thoroughly, centrifuged at 8,000 rpm to remove the sediment, and then filtrated by the 0.45 μm filter.

The First DEAE Anion Exchange Chromatography

A first DEAE column is equilibrated by Tris buffer (pH 7.8) containing 6 mol/L urea. The solution from step (1) is loaded onto the DEAE column at a flow rate of 10 ml/min. Tris buffer (pH 7.8, conductivity 3.7 ms/cm) with a urea concentration of 6 mol/L is used to elute the column. ApoA-1 is eluted. The eluted volume is 10 L. Tris buffer (pH 7.8, conductivity 80.3 ms/cm) is used to elute the column, and the impurities are eluted.

The Second DEAE Anion Exchange Chromatography

The apoA-1 eluted in step 2 (pH 7.8, conductivity 3.7 ms/cm), containing apoA-1, urea and slight amount of impurities, is diluted with water by 5 fold and loaded onto the second DEAE column at a flow rate of 10 ml/min. The apoA-1 and a slight amount of impurities are combined to the column, and urea remains in the solution and is eliminated as flow-through.

Tris buffer without urea (pH 7.8, conductivity 12.2 ms/cm) is used to elute the column, and the impurities are eluted off the column. Then, Tris buffer without urea (pH 7.8, conductivity 50.4 ms/cm) is used to elute the column, and apoA-1 is eluted off.

The SDS-PAGE electrophoresis results are shown in FIG. 5. The results show that pure apoA-1 can also be acquired in a pilot scale process.

Example 5

ApoA-1 Protein Determination

The apoA-1 protein purified in Example 1 is determined by an apoA-1 immunoturbity determination kit from Shanghai SUN Biotech Co. LTD.

10 μl of purified protein is added to 1 ml of apoA-1 antiserum, and then incubated at 37° C. for 15 minutes. After incubation, the solution is detected by 505 nm absorbency. The results show that this protein is apoA-1.

Example 6

ApoA-1 Protein Determination

Using the method described in Example 5, the apoA-1 proteins from Examples 2 and 3, respectively, and the apoA-1 protein from Example 4 are detected by the apoA-1 immunoturbity determination kit from Shanghai SUN Biotech Co. LTD.

Similar results are obtained.

Figure 8:
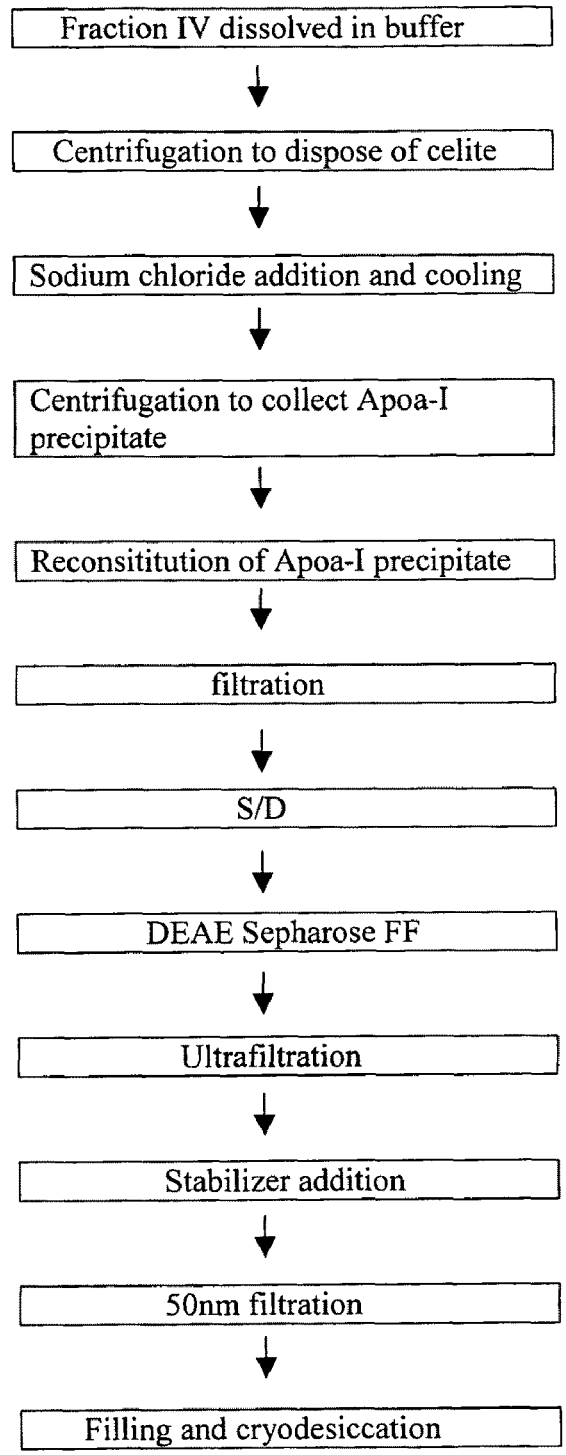
FIG. 8 is a flow chart showing an alternate production process according to the present invention of apoA-1 from plasma fraction IV.

An alternate embodiment of the process according to the present invention is illustrated in FIG. 8, which is a flow chart showing the production process of apoA-1 from plasma fraction IV.

The fraction IV is acquired by the Cohn Ethanol Fractionation method, as was described earlier herein in connection with the first-described process according to the present invention. The fraction IV is dissolved in a buffer, such as Tris buffer, phosphate buffer or HEPES buffer, preferably Tris buffer, to produce a pretreatment solution. The buffer pH is 7.2-8.5, preferably 7.5-8, and more preferably 7.8.

The pretreatment solution is centrifuged to remove celite. The centrifuge speed is 6,000-10,000 revolutions per minute (rpm) preferably 8,000 rpm. NaCl is added to the pretreatment solution to a final concentration of 2%, the pH of the pretreatment solution is adjusted to the range of from about 5.8 to about 6.0, and the pretreatment solution is cooled to −5 to 0 degrees C.

After cooling, the pretreatment solution is centrifuged again to collect the apoA-1 precipitate. The centrifuge speed is 6,000-10,000 rpm, preferably 8,000 rpm. The apoA-1 precipitate is reconstituted by dissolving it in about 30 times its volume of WFI (Water For Injection), and the reconstituted apoA-1 is kept at a temperature of about 10 to about 20 degrees C. The reconstituted apoA-1 is filtered by passing it through a filter having a pore size of 0.2-0.6 μm, preferably 0.45 μm. The filter removes the nonsoluble substances. The filter is washed with WFI after use.

An S/D (solvent/detergent) step is done by adding Tween 80 (a nonionic surfactant and emulsifier derived from polyethoxylated sorbitan and oleic acid) to a concentration of about 1.17% and TNBP (tri(n-butyl)phosphate) to about 0.3% and keeping the mixture at about 25 degrees C. for about 6 hours. Tween is a registered trademark of ICI Americas, Inc.

The filtered reconstituted apoA-1 is diluted with water by 1-10 fold, preferably 3-7 fold, and is loaded to a DEAE (Diethylamino Ethanol) Sepharose FF anion exchange column at a flow rate of 0.5-1.5 ml/min, preferably 0.8-1.2 ml/min. Protein in the diluted filtered reconstituted apoA-1, including the apoA-1, is combined onto the column.

Then, the protein on the column is eluted first by a buffer containing 1-8 M urea, preferably 3-7 M urea, and more preferably 5-6 M to elute apoA-1, and secondly by a buffer with high conductivity to protein mainly containing impurities. The eluent that elutes apoA-1 has a conductivity of 1-4 ms/cm, preferably 2-3.8 ms/cm, and more preferably 2.5-3.6 ms/cm. Salts in the eluent may include, but are not limited to, NaCl, KCl, $MgCl_2$ and $CaCl_2$. NaCl is preferred. The eluent that elutes impurities contains 0-1 M urea; 0 M is preferred. The conductivity is 4.5-100 ms/cm. Salts in the eluent may include, but are not limited to, NaCl, KCl, $MgCl_2$ and $CaCl_2$. NaCl is preferred.

A buffer usually used in this field is chosen: Tris buffer, phosphate buffer or HEPES buffer, preferably Tris buffer. The buffer pH is 7.2-8.5, preferably 7.5-8, and more preferably 7.8.

The volume ratio of fraction IV and the column is 1:5-50, preferably 1:15-40, and more preferably 1:20-30.

In this invention, post processing methods are also provided to process the pure apoA-1 solution acquired by the steps recited thus far. The post processing methods include an ultrafiltration step, a stabilizer adding step, a further filtration step and a filling and cryodesiccation step. Freeze dried apoA-1 is ultimately acquired after post processing steps.

Ultrafiltration, which is frequently applied in this field, is used for apoA-1 solution conditioning, adjusting the solution to an appropriate pH, such as 7.00, and an appropriate protein concentration, such as 5.0%. For the ultrafiltration, a Millipore PES ultrafiltration membrane with a molecular weight cutoff of 5000 is used, the working temperature is 4° C., and the working pressure is less than 0.3 Mpa.

The stabilizer added is from among those frequently used in this field, including, but not limited to, hydroxypropyl cellulose, hydroxypropyl methylcellulose, sodium cellulose glycolate, sucrose, sorbierite, etc.

The further filtration step involves passing the stabilized solution through a filter having pores no larger than 50 nm to remove inactive viruses, preferably having pores of 20 nm for removing smaller virus particles and prions.

A freeze drying method that is frequently applied in this field is used: the product is filled into bottles, frozen below −36° C. for 3-4 hours, and then freeze dried under a vacuum of 7-9 Pa. The temperature in the cold trap is about −55° C., and then, in a second period, the shelf temperature is 40° C. and the time is about 15 hours.

The chromatography column used in this invention may be from among those frequently applied in this field, and the chromatography media may be QAE (quaternary amine) or DEAE anion exchange chromatography media, preferably DEAE.

Unless defined otherwise, the definitions of the technical or scientific terms are those generally understood by the technician of ordinary skill in this field.

It will further be appreciated by those skilled in the art and it is contemplated that variations to the embodiments illustrated and described herein may be made without departing from the spirit and scope of the present invention. Accordingly, it is intended that the foregoing description is illustrative only, and the true spirit and scope of the invention will be determined by the appended claims.

The invention claimed is:
1. A method of purifying apolipoprotein A-1, comprising:
 a) mixing plasma fraction IV with a solution of 1-8 M urea, forming a fraction IV pretreatment solution;
 b) loading the pretreatment solution acquired in step a) to a first anion exchange chromatography column, and then eluting with a buffer I comprising 1-8 M urea having a conductivity of 1-4 mS/cm to obtain an eluate I that mainly contains apoA-1 protein;

c) loading eluate I to a second anion exchange chromatography column, first eluting with a buffer II, having a conductivity of 1-15 mS/cm, and later eluting with a buffer III, having a conductivity of 30-100 mS/cm, to obtain pure apoA-1 protein.

2. The method of claim 1, wherein the plasma fraction IV is obtained by the Cohn ethanol fractionation method.

3. The method of claim 1, wherein buffer II includes 0-1 M urea.

4. The method of claim 1, wherein buffer III includes 0-1 M urea.

5. The method of claim 1, wherein the urea concentration in steps a) and b) is 3-8 M.

6. The method of claim 1, wherein the urea concentration in steps a) and b) is 5-7 M.

7. The method of claim 1, wherein the conductivity of buffer I is 2-4 mS/cm, the conductivity of buffer II is 7-15 mS/cm, and the conductivity of buffer III is 70-95 mS/cm.

8. The method of claim 1, wherein the conductivity of buffer I is 2.5-3.6 ms/cm, the conductivity of buffer II is 9-12 mS/cm, and the conductivity of buffer III is 80-90 mS/cm.

9. The method of claim 1, wherein each anion exchange chromatography column is one of 1) a strong anion exchange chromatography column and 2) a weak anion exchange chromatography column.

10. The method of claim 1, wherein each anion exchange chromatography column is one of 1) a QAE ion exchange column and 2) a DEAE ion exchange column.

11. The method of claim 1, wherein, between steps b) and c), most impurities are eluted by a buffer IV having a conductivity of 4.5-70 mS/cm.

12. The method of claim 1, further comprising, after step c), at least one of ultra filtering the pure apoA-1 protein, adding a stabilizer to the pure apoA-1 protein, and lyophilizing the pure apoA-1 protein.

13. A method of purifying apolipoprotein A-I, comprising:
a) dissolving plasma fraction IV in a buffer to produce a fraction IV pretreatment solution;
b) centrifuging the pretreatment solution to remove celite;
c) adding NaCl to the pretreatment solution and cooling the pretreatment solution to form apoA-1 precipitate;
d) again centrifuging the pretreatment solution, to collect the apoA-I precipitate;
e) reconstituting the apoA-I precipitate;
f) filtering nonsoluble substances from the reconstituted apoA-1;
g) loading the reconstituted apoA-1 to an anion exchange chromatography column to combine protein in the reconstituted apoA-I, including apoA-I, onto the column; and
h) eluting apoA-I from the column with a buffer.

14. The method of claim 13, wherein the plasma fraction IV is obtained by the Cohn ethanol fractionation method.

15. The method of claim 13, wherein the apoA-I on the column is eluted by a buffer containing 1-8 M urea.

16. The method of claim 15, wherein the protein on the column that mainly contains impurities is eluted by a buffer having a conductivity of 4.5-100 mS/cm to elute protein.

17. The method of claim 13, further comprising ultrafiltering the apoA-I eluted from the column with an ultrafiltration membrane having a molecular weight cutoff of 5000.

18. The method of claim 17, further comprising passing the ultrafiltered apoA-I through a filter having pores no larger than 50 nm.

19. The method of claim 17, further comprising passing the ultrafiltered apoA-I through a filter having pores of 20 nm.

20. The method of claim 13, further comprising freeze drying the apoA-I eluted from the column.

21. The method of claim 13, wherein the NaCl added to the pretreatment solution is added to a concentration of 2%.

22. The method of claim 13, wherein the step of cooling comprises cooling the pretreatment solution to −5 to 0 degrees C.

23. The method of claim 13, wherein the step of reconstituting comprises reconstituting the apoA-I precipitate in about 30 times its volume of water for injection.

24. The method of claim 13, wherein the step of filtering comprises passing the reconstituted apoA-I through a 0.45/*m filter.

25. The method of claim 13, further comprising, between the steps of filtering and loading, adding polyoxyethylene sorbitan monooleate to the reconstituted apoA-I to a concentration of about 1.17% and tri(n-butyl)phosphate to about 0.3%, and keeping the mixture at about 25 degrees C. for about 6 hours.

26. The method of claim 13, further comprising, before the step of loading, diluting the reconstituted apoA-1 with water by 1-10 fold.

27. The method of claim 26, wherein the step of loading comprises loading the diluted, reconstituted apoA-1 to a diethylamino ethanol anion exchange column at a flow rate of 0.5-1.5 ml/min.

28. The method of claim 15, wherein the buffer that elutes apoA-1 has a conductivity of 1-4 mS/cm.

29. The method of claim 13, wherein the pH of the pretreatment solution is adjusted to the range of from about 5.8 to about 6.0.

30. The method of claim 13, wherein the reconstituted apoA-I is kept at a temperature of about 10 to about 20 degrees C.

31. The method of claim 1, wherein the mixing to form a pretreatment solution includes adding a buffer having a pH range of from about 7.2 to about 8.5.

32. The method of claim 1, further comprising diluting the pretreatment solution 1 to 10 fold with water prior to loading onto the first anion exchange chromatography column.

33. The method of claim 13, wherein the centrifuging steps occur at a centrifuge speed of about 6,000 to about 10,000 rpm.

* * * * *